United States Patent [19]

Hamlin

[11] Patent Number: 4,921,618
[45] Date of Patent: May 1, 1990

[54] INVERTED SEPARATION AND TRANSFER DEVICE, AND PROCESS FOR USING SAME

[75] Inventor: Jack A. Hamlin, Proctorville, Ohio
[73] Assignee: BASF Corporation, Parsippany, N.J.
[21] Appl. No.: 68,305
[22] Filed: Jul. 1, 1987
[51] Int. Cl.⁵ .......................................... B01D 45/02
[52] U.S. Cl. .................................. 210/780; 210/782
[58] Field of Search ............. 210/359, 398, 399, 460, 210/472, 514, 516, 518, 780, 782

[56] References Cited

U.S. PATENT DOCUMENTS

| | | | |
|---|---|---|---|
| 3,300,051 | 1/1967 | Mitchell | 210/472 X |
| 3,481,477 | 12/1969 | Farr | 210/359 |
| 3,493,503 | 2/1970 | Mass | 210/460 X |
| 3,788,483 | 1/1974 | Conway | 210/472 X |
| 3,932,277 | 1/1976 | McDermott et al. | 210/780 |
| 3,955,423 | 5/1976 | Ohringer | 210/359 X |
| 3,969,250 | 7/1976 | Farr | 210/359 |
| 4,021,352 | 5/1977 | Sarstedt | 210/359 |
| 4,035,150 | 7/1977 | Jaffe | 210/359 X |
| 4,209,488 | 6/1980 | Breno | 210/359 X |
| 4,210,623 | 7/1980 | Breno et al. | 210/359 X |
| 4,357,240 | 11/1982 | Mehra et al. | 210/472 X |
| 4,464,254 | 8/1984 | Dojki et al. | 210/359 X |
| 4,485,015 | 11/1984 | Smith | 210/472 X |
| 4,487,696 | 12/1984 | Ferrara | 210/399 |
| 4,522,713 | 6/1985 | Nussbaumer et al. | 210/472 X |
| 4,525,276 | 6/1985 | Toda et al. | 210/472 X |
| 4,587,221 | 5/1986 | Cais et al. | 210/359 X |
| 4,602,995 | 7/1986 | Cassaday et al. | 210/359 X |
| 4,643,981 | 2/1987 | Card | 210/780 X |
| 4,675,110 | 6/1987 | Fay | 210/472 X |

Primary Examiner—Robert Spitzer
Attorney, Agent, or Firm—Rupert B. Hurley, Jr.

[57] ABSTRACT

A device and process for simultaneous separation and transfer utilizes an inverted device which holds a liquid, to be separated, above a collection cup. Preferably the separation is accomplished by filtration. The separation and transfer occur without spillage or contamination of the liquid. The device and process are especially useful for the filtration of liquid samples prior to analysis via gas chromatography or high pressure liquid chromatography.

11 Claims, 4 Drawing Sheets

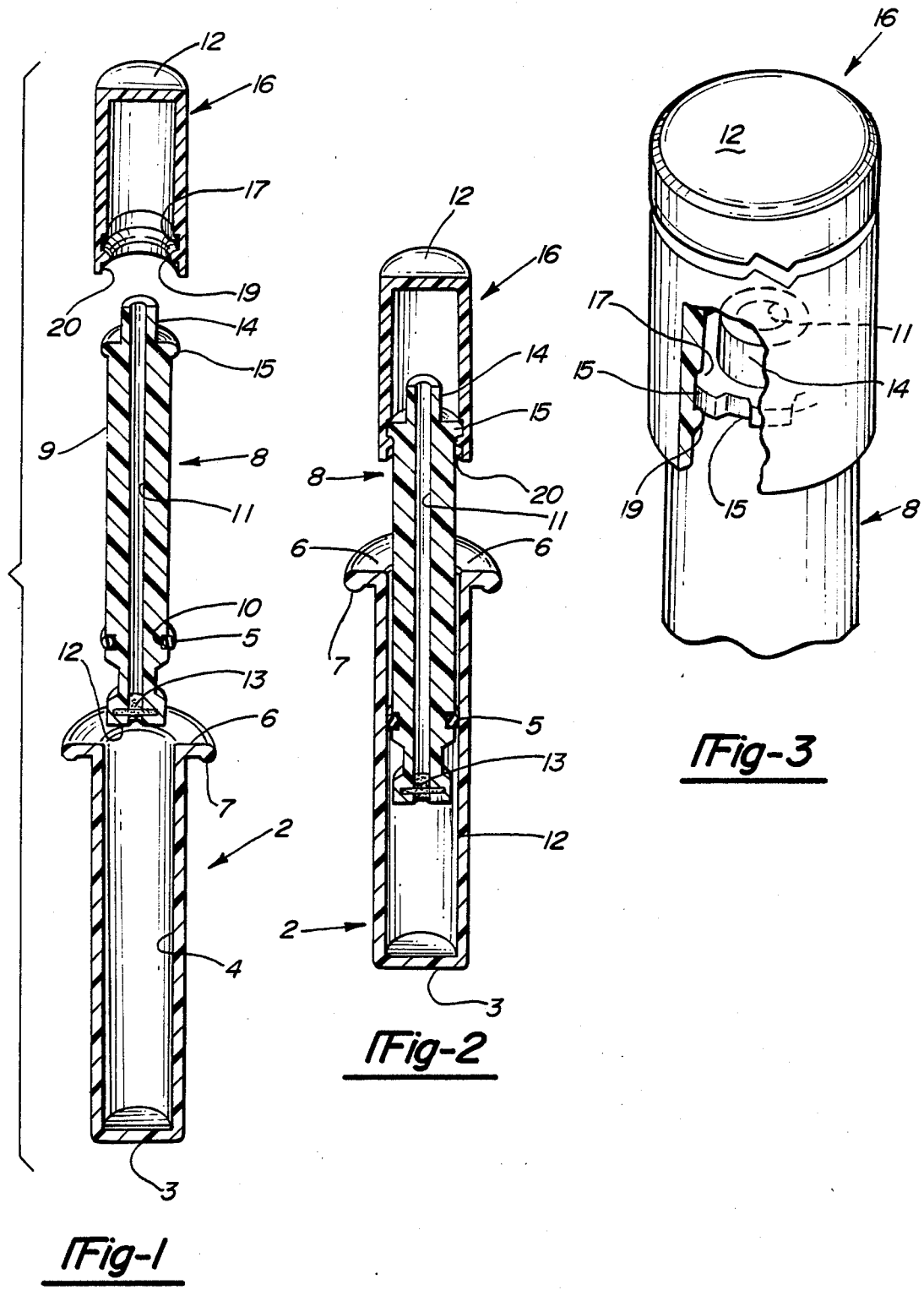

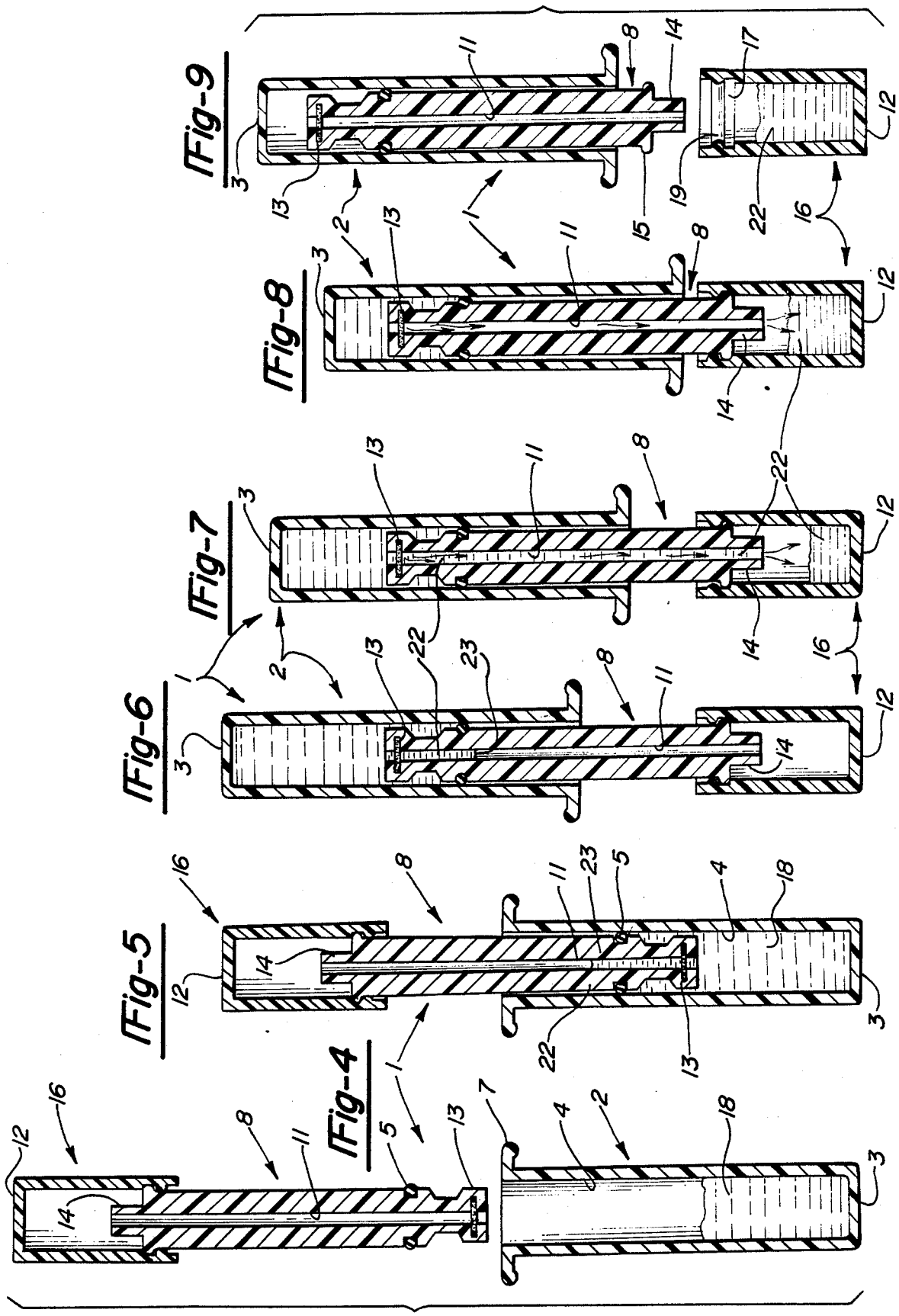

INVERTED SEPARATION AND TRANSFER DEVICE, AND PROCESS FOR USING SAME

BACKGROUND OF THE INVENTION

1. Field of the Invention

The present invention pertains to an apparatus and process for liquid purification or separation, and also for liquid transfer. Although the invention can be used for liquid-liquid separations, the present invention is most useful in the purification of liquids by filtering small solid particulates from the liquid. The invention utilizes a moveable medium for the filtration process. In addition to the separation of the components of a mixture, the present invention enables one to simultaneously separate a liquid from a mixture while transferring the separated liquid to another container without risk of spillage or contamination of the separated liquid.

2. Description of the Prior Art

U.S. Pat. No. 3,955,423 (hereinafter the '423 patent) is the first of two U.S. patents which the applicant considers to be the closest art with respect to the present invention. The subject matter of the '423 patent involves a device " . . . for isolating a liquid sample from a specimen container . . . ." The '423 patent utilizes an elongated cylindrical collection tube which terminates, on its lowermost end, with a filter means. The cylindrical collection tube slides in sealed contact with the inner surface of a specimen container which is holding a liquid sample. On the uppermost end of the cylindrical collection tube is an air escape notch or opening and still further above, a collection cup serves as a protective cap for the uppermost end of the collection tube. Although the device of the '423 patent is closely related to the device of the present invention, several important distinctions between the '423 patent teachings and the device and process of the present invention can be made, as follows:

(1) In the '423 patent, filtration cannot be accomplished while the apparatus is in an inverted position, without creating spillage and/or operability problems; and (2) and device of the '423 patent requires that the filtration step take place while the apparatus is in an upright position (i.e. the specimen tube remains lowermost). after which the apparatus is inverted for the transfer step.

In contrast, the apparatus and process of the present invention solves problems associated with the device taught in the '423 patent. First, as is discussed in detail below, the device and process of the instant invention permit both filtration and transfer to be carried out while the device is "inverted", without permitting either spillage, contamination or operability problems. Secondly, the device and process of the instant invention permit the escape of displaced gas (i.e. air) during the filtration process, without permitting spillage of filtered liquid. Third, the device and process of the instant invention permit filtration while substantially eliminating potential contamination due to exposure to the atmosphere. The solution to these three problems permits an easier filtration and transfer of liquid without risk of spillage or contamination. Furthermore, the device and process of the present invention are significantly less complicated than both the device and process taught in the '423 patent.

Also relevant to the present invention is U.S. Pat. No. 3,481,477 (hereinafter the '477 patent). The '477 patent teaches an apparatus for filtering/separating liquids. The apparatus has an outer tubular member within which slides a hollow plunger which has a sealed fit with the interior surface of the tubular member. The hollow plunger has a filter therein. After the liquid being filtered proceeds a very short distance into the plunger, it is immediately forced into a tube of small diameter which is concentrically arranged within the plunger. The tube directs the filtered liquid up and out of the other end (i.e. the upper end) of the plunger and then down and into a separate vial. The subject matter of the '477 patent differs from the subject matter of the present invention in many ways, several of which are described as follows:

(1) In the '477 device, the collection vial is completely unconnected to the plunger, whereas in the instant invention there is contact between the plunger and the collection vial;

(2) the device of the '477 patent is not substantially encased, resulting in the potential for spillage, release of dangerous volatile components, and sample contamination, while, in contrast, the device of the present invention provides for substantial encasement of the components being handled, reducing the risk of spillage, release of dangerous volatile components, and sample contamination. while permitting the escape of displaced gas; and (3) the device of the '477 patent requires alignment of the receiving vessel (19) and the flexible tubing (15). This alignment can be disturbed by the movement of plunger tube (12), whereas the device of the present invention has no similar critical alignment.

Applicant is aware of still further prior art U.S. patents including the following: U.S. Pat. Nos. 4,300,404; 4,210,623; and 3,969,250. Although these patents are also related to the present invention, applicant contends that they are not closely related enough to deserve any detailed discussion regarding the patentability of the present invention. None of the prior art referred to herein teaches simultaneous filtration and transfer utilizing an inverted device.

In summary, although each of the advantages of the present invention over the technology described in the prior art is important, the combination of advantages of the present invention, along with its simplicity of design and ease of manufacture, make it especially advantageous for the separation of components from mixtures.

BRIEF SUMMARY OF THE INVENTION

The handling, filtration, and transfer of mixtures which contain at least one liquid phase is a practice which has been carried out with great frequency in the past. The manipulation of these "liquid mixtures" inherently involves the potential for spillage of the liquid and contamination of the liquid. These potential problems are especially acute when the liquid phase being isolated will be subjected to chemical or physical analysis. Complex modern chemical analyses (e.g. high pressure liquid chromatography, gas chromatography, and mass spectrometry) are sensitive to contamination of the liquid phase. Furthermore, these samples often involve the use of volatile and dangerous solvents. The majority of the liquid phase being isolated is usually an organic solvent, and in many cases these organic solvents are hazardous liquids having toxic properties. The handling of samples prior to analysis often requires filtration and transfer of these liquids. In our ever-increasing sophistication and diversity of chemical, biological, and physical analyses, it is apparent that the number of samples being analyzed has been, and will continue to be, increasing expotentially. In addition, the increasing sensitivity of these analyses continues to make them more sensitive to external contamination and imperfect isolation. Thus there is a strong need for efficiency, simplicity, safety, and reliability in the handling of both mixtures and isolated liquid phases which will be subjected to analysis. The present invention addresses all of these needs, in that the present invention supplies an efficient, simple, safe, and reliable apparatus and process for the handling and isolation of samples and sample components prior to their analysis.

The apparatus of the present invention comprises a container tube for holding a desired quantity of a liquid. The container tube has an inner cross-section which is substantially uniform along the longitudinal axis of the container tube. The apparatus further comprises an openended, tubular plunger, the lower end of which has a means for forming a liquid-tight seal with the interior surface of the container tube, thus permitting the seal to be maintained while the plunger slides within and along the axis of the container tube. The apparatus further comprises a collection cup, which, after the apparatus is completely assembled, filled, and inverted, is positioned below the plunger while the plunger is being depressed. Thus, the liquid traveling through the tubular plunger flows downward and into the collection cup. The junction between the collection cup and the plunger allows the passage of displaced gas therethrough during the depression of the plunger. The apparatus further comprises means for insuring that substantially all of the liquid passing completely through the tubular plunger is deposited directly into the collection cup. Part of this means is found in the junction between the tubular plunger and the collection cup. In combination with the above elements, in one embodiment the apparatus is designed so that the plunger can be depressed by applying force to both the liquid receiver container and the container tube.

The combination of features produces a device and process increasing the efficiency, simplicity, safety, and reliability of sample preparation prior to analysis. Most importantly, the device is especially suited to being used in a device for simultaneously filtering and transferring a large number of samples.

The process of the present invention is a process for separating a mixture which comprises at least one liquid phase. The process comprises filling a container tube with a desired quantity of a mixture which comprises a liquid, followed by inserting a tubular plunger into the container tube so that the plunger forms a liquid-tight seal with the container tube. If the now "upper end" of the plunger does not have a collection cup attached thereto, a collection cup should now be attached to the top of the plunger. The resulting assembly is then inverted with substantially all of the liquid remaining above the plunger. Lastly, the separation process is carried out by forcing the hollow plunger along the axis of, and a desired distance further into, the container tube, whereby a desired quantity of the liquid flows down through the plunger and into the container tube. Simultaneously, displaced gas, initially within the collection cup and the plunger, is allowed to escape from the device during passage of liquid through the tubular plunger and into the collection cup.

The process described above, although applicable to the separation of a liquid phase from liquid-liquid mixtures, is most preferably utilized in separating a liquid phase from a mixture comprising the liquid phase and solid particulates. This preferred process is accomplished by additionally filtering the mixture as the mixture flows into the tubular plunger. Thus, in the preferred process, a mixture comprising a liquid with solid particulates therein is both filtered and transferred by the movement of the plunger into the container tube. Of course, the process requires that this be done without spillage and with venting of air displaced by the shrinking volume within the assembly.

BRIEF DESCRIPTION OF THE DRAWINGS

FIG. 1 is an exploded, cross-sectional view of the device of the present invention.

FIG. 2 is a cross-sectional view of the assembled device of the present invention.

FIG. 3 is an enlarged, detailed, perspective view of the junction between the plunger (8) and the collection cup (16).

FIGS. 4, 5, 6, 7, 8, and 9 are longitudinal cross-sectional views of the device during different stages of the process of operating the device. These figures also include a liquid sample which is filtered during the operation of the device.

DETAILED DESCRIPTION OF THE PREFERRED EMBODIMENTS

Figure 10:
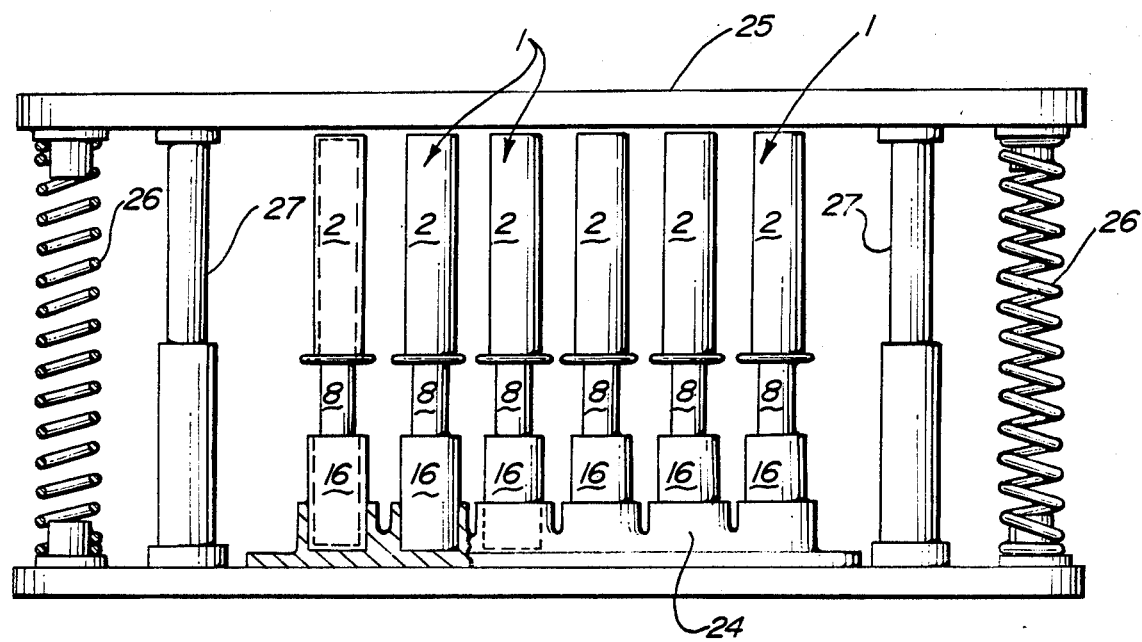
FIGS. 10, 11, and 12 are cross-sectional views of a multiplicity of filtration/transfer devices which are in successive stages of the filtration/transfer process. Also shown in FIGS. 10, 11, and 12 is a press device which may be utilized to put force on each of the filtration/transfer assemblies in order to simultaneously operate a plurality of filtration/transfer assemblies of the apparatus of the present invention.

The apparatus of the present invention is comprised of several components which are each illustrated in FIG. 1. As shown in FIG. 1, a container tube (2) has a closed bottom (3) and an interior wall (4) which creates a uniform cross-sectional area along the length of the container tube. The container tube has an open upper end (6), and most preferably has a lip (7) associated therewith.

The apparatus of the present invention further comprises a plunger (8). The plunger is made up of a hollow main shaft (9), and further comprises an indented section (10) for holding an O-ring (5) therein. The plunger (8) and its associated O-ring (5) are sized to form a liquid-tight seal with the interior surface :(4) of the container tube (2). This seal is maintained while the plunger slides within the tube. The tubular plunger has an inner surface (11) which provides a passageway through the plunger. In the most preferred embodiment of the apparatus of the present invention, near the lower end (12) of the plunger, a filter means (13) is positioned across the passageway through the plunger, so that all materials passing completely through the plunger must pass through the filter means (13). The most preferred embodiment of the plunger (8) has a tip portion (14). The tip portion (14) has an outside diameter significantly smaller than the outside diameter of the shaft portion (9), in order to keep liquid (emerging from the passageway through the plunger) clear of the junction between the plunger and a collection cup (16). Adjacent the tip portion (14), the shaft section terminates in a protrusion (15), the protrusion (15) providing a means for reversibly securing the plunger (8) to the liquid collection cup (16). The protrusion (15) may be either a single ring-like portion of the plunger, or the protrusion may be a multiplicity of nodules, either embodiment of which can enable a snap fit of the plunger (8) to the collection cup (16), as is described in detail below. The collection cup (16) is most preferably a cuplike structure which has a flat bottom (12). The cup (16) is sized in order to both: (1) accept a desired quantity of material passing through the plunger; and (2) have enough additional volume to accept as much of the plunger portion as is required when the plunger portion is coupled to the collection cup, so that the tip portion (14) of the plunger remains above the surface of liquid deposited in the collection cup (16). Furthermore, the collection cup (16) most preferably comprises an annular groove (17) for acceptance of the protrusion (15) on the plunger (8). As shown in FIG. 1, a lowermost inner surface (20) within the collection cup (16) is bounded above by an annular protrusion (19), which protrusion (19) is, in turn, bounded immediately above by the annular groove (17). The combination of the protrusion or nodes (15) on the plunger with the annular protrusion (19) and annular groove (17) of the collection cup together permit a reversible snap fitting of the plunger with the collection cup.

The junction formed by the protrusions (15 and 19) together with the groove (17) must be designed so that a means for allowing displaced gas to escape while simultaneously preventing either (1) a spillage of material through the junction or (2) any substantial contamination to enter the assembled apparatus. The degree of prevention of spillage as well as the degree of prevention of contamination by outside materials is, of course, dependent upon the criticality of spillage and contamination for the materials being handled within the apparatus. Thus, more sophisticated means for complete prevention of chemical, biological, and other contamination and spillage may be incorporated into the junction. However, for many uses, such as the preparation of samples for high pressure liquid chromatography, a junction such as the one enabled by the structure of FIG. 3 is completely satisfactory.

In the junction between the plunger and the collection cup, the means for permitting air displaced during the operation of the device (i.e., during transfer, and, if desired, filtration) can be achieved by making protrusion (15) incomplete (i.e., not permitting protrusion (15) to extend continuously around the plunger). This is illustrated in FIG. 3. Furthermore, protrusion (19) may also be made incomplete, especially in the event that the protrusion (19) fits snugly against the outer surface of the shaft (9) of the plunger (8). A combination of an incomplete protrusion (15) and an incomplete protrusion (19) will provide a path of escape for displaced air during operation of the apparatus. However, the degree of discontinuity cannot be so large that the coupling of the plunger (8) and the collection cup (16) is insecure.

FIG. 2 illustrates a cross-sectional view of the assembled device (1). As is shown in FIG. 2, upon assembly of the container tube (2), the plunger (8), and the collection cup (16), the O-ring (5) forms a seal with the inner wall (4) of the container tube. In addition, the coupling of the plunger with the collection cup is enabled by first forcing the protrusion (15) to travel within and over the annular protrusion (19) within the collection cup (16), after which the protrusion (15) fits into the groove (17).

FIGS. 4 through 9 illustrate the device of the present invention during the process of its operation. The device and process are both directed towards the simultaneous separation and transfer of a sample mixture. The container tube (2) is first filled with a desired quantity of the mixture (hereinafter termed sample 18). as shown in FIG. 4. Most preferably, a plunger/collection cup assembly (16 and 8) is then inserted into the container tube, the plunger being placed into sealed engagement with the inner surface (4) of the collection tube (2), by forcing the O-ring (5) against the inner wall (4) of the collection tube (2), resulting in the configuration shown in FIG. 5. The procedure creates a liquid-tight seal between the plunger and the container tube. In FIG. 5, the plunger has been forced far enough into the collection tube that a small fraction of the sample (18) has entered the passageway through the plunger, and a small portion of the sample (18) has passed through the filter (13), resulting in a filtered liquid (22) above the filter (13), the filtered liquid (22) rising to the level of a meniscus (23). The entire assembly (1) is then inverted, resulting in the stage shown in FIG. 6. Upon inversion, most of the liquid is above the plunger.

FIG. 6 illustrates a point in the process at which both filtration and transfer can be simultaneously performed. The simultaneous filtration and transfer of a desired quantity of sample (18) is shown by the stages illustrated in FIGS. 7 and 8. To accomplish the simultaneous filter and transfer, the plunger is merely forced further into the collection tube, forcing the sample (18) to pass through the filter and the passageway, and to be deposited within the collection cup. As can be seen by an examination of FIGS. 7 and 8, the extension of the tip portion (14) of the plunger effectively prohibits spillage of the filtered liquid (22) through the junction between the plunger (8) and the collection cup (16).

Once a desired quantity of filtered liquid (22) has been both separated and deposited in the collection cup, the collection cup may then be detached from the remainder of the assembly, as shown in FIG. 9. The snap-fitting type of coupling between the plunger and the container cup allows this to be easily performed, without risk of spillage. Furthermore, it has been found that the filtered liquid (22) remaining within the passageway through the plunger, after a desired amount of filtration has occurred, does not drip from the container tube/plunger assembly if the detachment of the collection cup (16) is performed with reasonable handling. Thus spillage of the liquid is prevented, while at the same time, transfer of the filtered liquid to the collection cup was also performed without risk of spillage.

Figure 11:
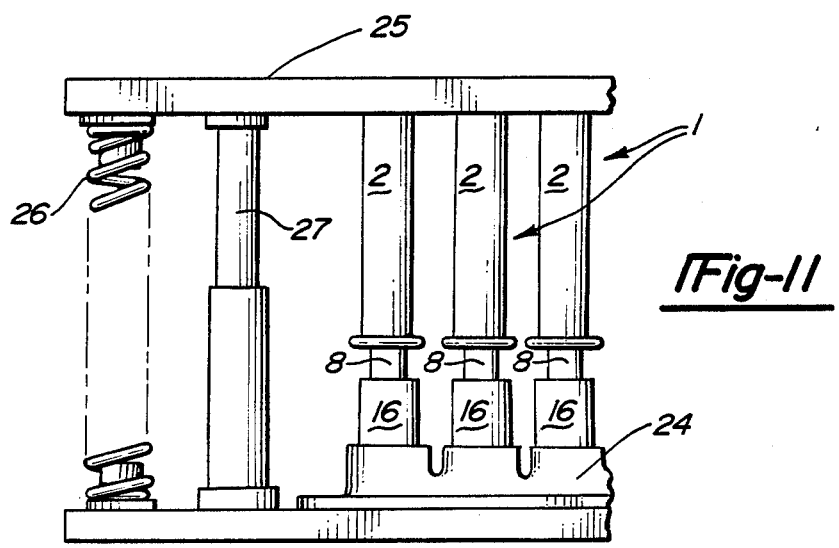
Figure 12:
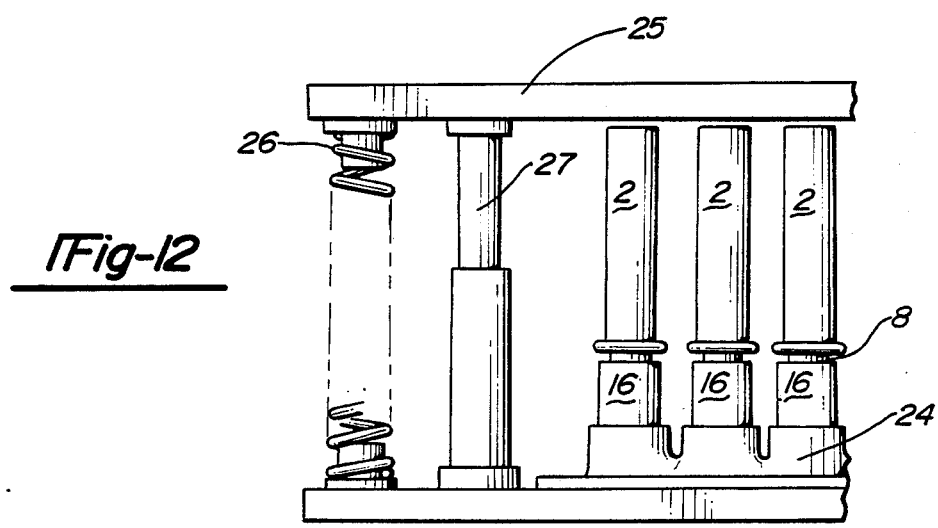

FIGS. 10, 11, and 12 each illustrate a cross-sectional view of six filtration/transfer assemblies (1) which have been placed in a rack (24), with the rack, having assemblies therein, then being placed within a press (25). The press utilizes springs (26) to force the plunger further into the container tube so that filtration and transfer are simultaneously carried out. After a desired amount of filtration is performed, pistons (27) are activated so that pressure on the assemblies is terminated, and so that the assemblies (1) together with the rack (24) can be removed from the press. FIG. 10 illustrates the assemblies (1) in the rack (24) immediately after they have been placed in the press (25), but before the assemblies (1) have been put under any pressure by the press. FIG. 11 illustrates a point further on in the process, wherein a portion of the desired filtration and transfer has been carried out. FIG. 12 illustrates the assemblies (1) in the rack (24) after the desired amount of filtration and transfer has been completed. As shown in FIG. 12, the pistons (27) have removed pressure from the assemblies (1), in order to terminate filtration and transfer, and in order to allow the rack and assemblies to be removed from the press. The collection cup (16) may be an auto-sampler vial, and the device for applying pressure to cause filtration and transfer may be designed for installation into an analytical instrument, such as an auto-sampler for use in a high pressure liquid chromatograph.

The apparatus and process of the present invention enable the processes of separation and transfer to be carried out on a mixture which comprises at least one liquid phase. Most preferably, solid particulates are in admixture with the liquid phase. In this most preferred embodiment, the solid particulates are removed from the mixture by a filter medium. However, the device and process of the present invention have also been comprehended for use in the separation and transfer of at least two continuous and separate liquid phases. For example, a mixture of oil and water wherein both phases are continuous (e.g., as in a separatory funnel) can be separated by the apparatus and process of the present invention.

Figure 13:
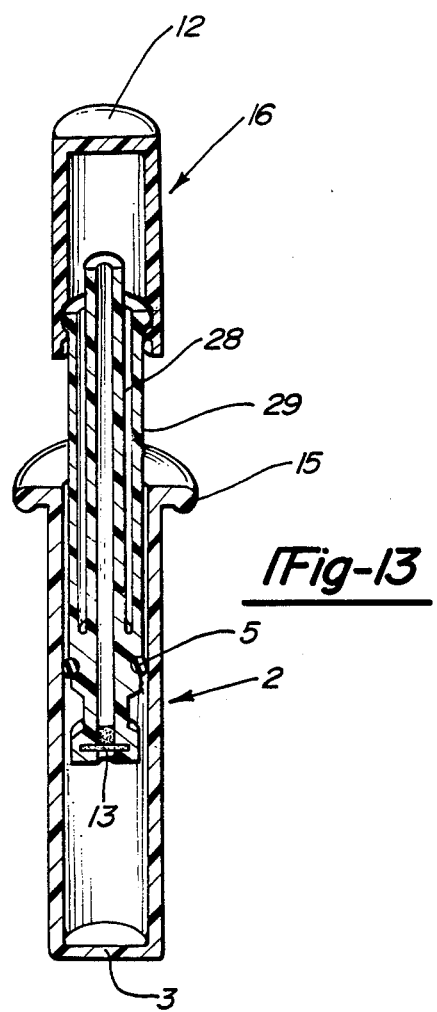
FIG. 13 is a longitudinal, cross-sectional view of an alternative device of the present invention.

FIG. 13 illustrates an alternative embodiment of the apparatus of the present invention. In this alternative, the device utilizes a tube (28) in order to prevent spillage of filtered liquid during the filtration/transfer step. The use of a separate tube decreases the amount of material required to construct the device, as the combination of the "thin-walled" plunger (29) and the tube (28) requires less material than the "thick-walled" plunger (8), illustrated in FIG. 1.

Figure 14:
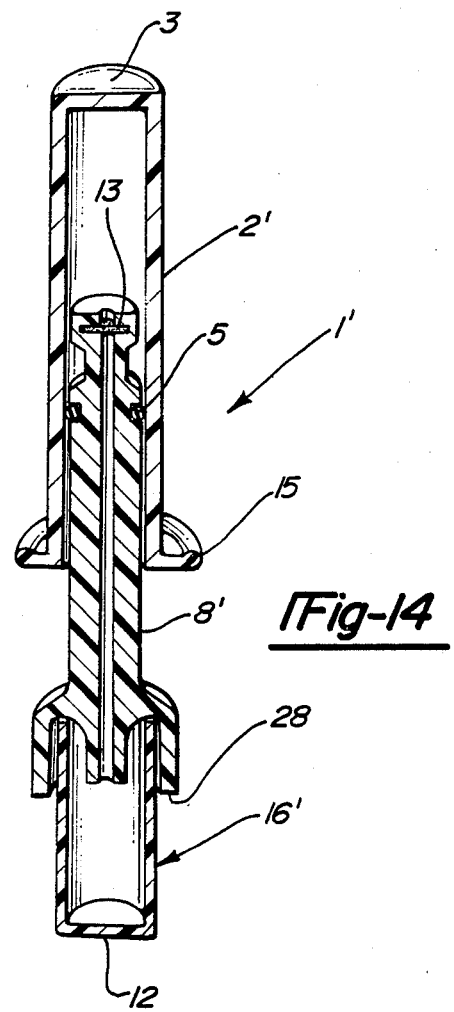
FIGS. 14 and 15 illustrate cross-sectional views of an alternative embodiment of the apparatus of the present invention.
Figure 15:
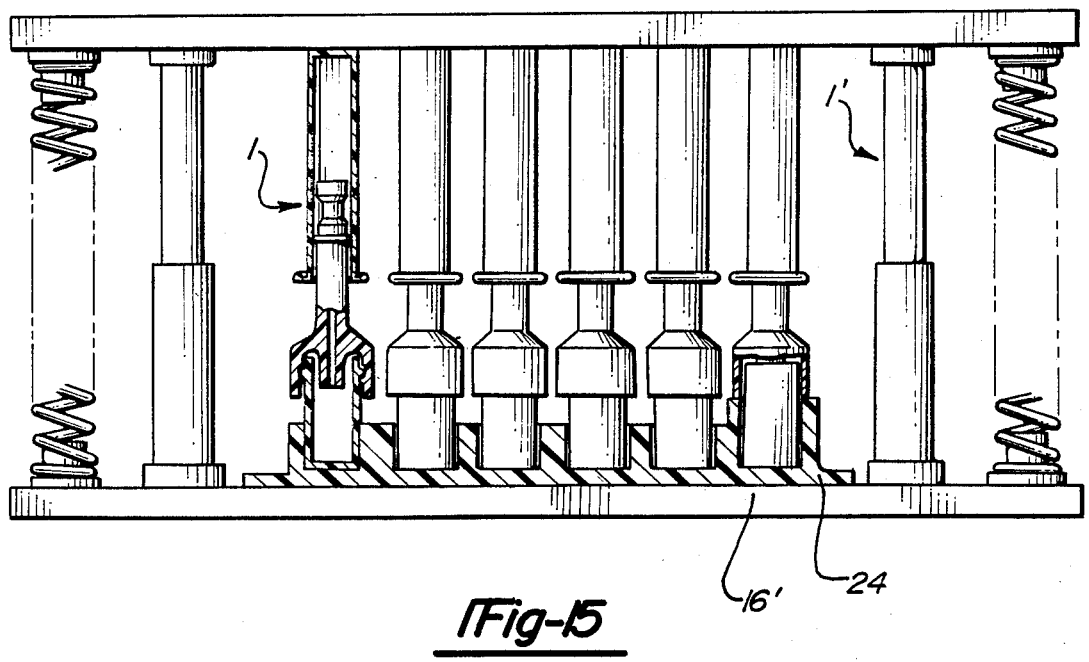

FIG. 14 illustrates an alternative embodiment (1') of the present invention. This embodiment differs from the embodiment shown in FIGS. 1–13 in that plunger (8') has an enlarged end (28) which permits simultaneous filtration and transfer to be carried out by utilizing means for applying force directly to the plunger (8') and the container tube (2'). FIG. 15 illustrates how device 1' can be installed and operated in a rack (24') which applies force directly to the plunger (8'), while avoiding applying pressure to the collection cup (16'). In FIG. 15 the rack (24) is designed to contact the enlarged end (28) of the plunger (8') so that no force is exerted on the container tube (16').

The device of the present invention simultaneously separates and transfers a liquid. The device is in an inverted position. The term "inverted" is descriptive of the device because the liquid to be separated is above the collection cup during separation and transfer. This is the source of the numerous advantages of the device and process invented, as well as the distinction between the invented device and process and the prior art.

The embodiments of the invention in which an exclusive property or privilege is claimed are defined as follows:

1. A process for separating a mixture, the mixture comprising a liquid, the process comprising the steps of:
   (a) filling a container tube with a desired quantity of the mixture;
   (b) inserting a tubular plunger into the container tube, the plunger forming a liquid-tight seal with the container tube:
   (c) inverting the tube-plunger assembly so that most of the liquid is above the plunger;
   (d) placing the lowermost end of the plunger within a collection cup container, a junction between the container cup and the lowermost end of the plunger providing a means for ensuring that substantially all of the liquid passing completely through the hollow plunger is deposited directly into a collection cup; and
   (e) forcing the hollow plunger along the axis of and further into the container tube, the junction between the collection cup and the plunger also permitting a gas which is initially within the liquid receiver container and collection cup to easily escape during passage of liquid through the tubular plunger and during deposition of the liquid into the collection cup, whereby simultaneous separation and transfer occur.

2. A process for separating a mixture as described in claim 1, wherein the mixture comprises a liquid phase having solid particulates therein.

3. A process for separating a mixture as described in claim 1, the mixture comprising at least two separate liquid phases.

4. A process for separating a mixture as describe in claim 1, wherein the mixture comprises a liquid which is an organic solvent.

5. A process for separating a mixture as described in claim 4 wherein the mixture additionally comprises solid particulates.

6. A process for separating a mixture as described in claim 1, wherein the mixture comprises a volatile solvent.

7. A process for separating a mixture as described in claim 1, wherein the mixture comprises a liquid having solid particulates therein and the tubular plunger has a filter located within so that all liquid passing through the tubular plunger is subjected to filtration.

8. A process for separating a mixture as described in claim 7, wherein the filtration process produces a filtered liquid which is suitable for use in high pressure liquid chromotography.

9. A process as described in claim 1 wherein the collection cup is an auto-sampler vial.

10. A process as described in claim 1 wherein force is applied directly to the container tube and the plunger so that simultaneous filtration and transfer occur without subjecting the collection cup to the force.

11. A process as described in claim 1 wherein force is applied to the container tube and the collection cup, so that simultaneous filtration and transfer occur.

* * * * *